(12) United States Patent
Parrish

(10) Patent No.: US 7,800,495 B1
(45) Date of Patent: *Sep. 21, 2010

(54) OPEN AND COVERT DETECTION MECHANISMS FOR MATERIALS AT LOCATIONS OF INTEREST

(76) Inventor: Warren G. Parrish, 3838 Warren Ridge St., Sarasota, FL (US) 34233

( * ) Notice: Subject to any disclaimer, the term of this patent is extended or adjusted under 35 U.S.C. 154(b) by 0 days.

This patent is subject to a terminal disclaimer.

(21) Appl. No.: 12/399,966

(22) Filed: Mar. 8, 2009

Related U.S. Application Data

(63) Continuation of application No. 11/390,402, filed on Mar. 27, 2006, now Pat. No. 7,522,041.

(60) Provisional application No. 60/666,127, filed on Mar. 29, 2005.

(51) Int. Cl.
*G08B 21/00* (2006.01)
(52) U.S. Cl. ............................................. 340/540
(58) Field of Classification Search ................ 340/540, 340/568.1, 539.22, 506, 555; 250/287; 356/72, 356/318
See application file for complete search history.

(56) References Cited

U.S. PATENT DOCUMENTS

| | | | |
|---|---|---|---|
| 5,141,312 A * | 8/1992 | Thompson et al. ........... 356/218 |
| 5,438,360 A | 8/1995 | Edwards | |
| 5,443,793 A | 8/1995 | Ehrlich et al. | |
| 5,652,651 A | 7/1997 | Dunne | |
| 5,760,898 A * | 6/1998 | Haley et al. ................. 356/318 |
| 6,201,493 B1 | 3/2001 | Silverman | |
| 6,773,674 B2 * | 8/2004 | Bannister et al. ............. 422/83 |
| 6,984,524 B2 * | 1/2006 | Nguyen et al. .............. 436/107 |
| 7,088,435 B2 * | 8/2006 | Brestel et al. ................. 356/72 |
| 7,180,418 B1 | 2/2007 | Willms et al. | |
| 2004/0008345 A1 | 1/2004 | Nurmikko et al. | |
| 2004/0220753 A1 | 11/2004 | Tabe | |
| 2005/0156734 A1 | 7/2005 | Zerwekh et al. | |
| 2006/0023211 A1 | 2/2006 | Gandhi et al. | |
| 2006/0249683 A1 | 11/2006 | Goldberg et al. | |

* cited by examiner

*Primary Examiner*—Phung Nguyen
(74) *Attorney, Agent, or Firm*—Eric D. Jorgenson, Esq.

(57) ABSTRACT

An optical receiving and data communications system for sensing materials of interest (e.g., drugs and/or explosives) in transportation systems such as buses, trucks, cars, trains, aircraft, and ships, and checkpoints such as building entrances, roadblocks, passenger boarding areas, and the like. The system can be included in the transportation system, and includes a fiber optic front end that focuses and/or concentrates light reflected from a target into the fiber filament for communication to an optical sensor. When the target is illuminated at a predetermined wavelength, a vapor plume and/or particulate matter associated therewith is energized such that change information is caused to occur and be received into the fiber system. The change information is communicated over a fiber communications network to a remote processing and analysis system for processing and analysis to determine its chemical components.

20 Claims, 14 Drawing Sheets

US 7,800,495 B1

OPEN AND COVERT DETECTION MECHANISMS FOR MATERIALS AT LOCATIONS OF INTEREST

CROSS-REFERENCE TO RELATED APPLICATIONS

This application is a Continuation of pending U.S. patent application Ser. No. 11/390,402 entitled "OPEN AND COVERT DETECTION MECHANISMS FOR MATERIALS AT LOCATIONS OF INTEREST" and filed Mar. 27, 2006, which claims the benefit of U.S. Provisional Patent application Ser. No. 60/666,127 entitled "OPEN AND COVERT DETECTION MECHANISMS FOR A CHEMICAL COMPOSITION DETECTION SYSTEM" and filed Mar. 29, 2005.

This application is related to copending U.S. patent application Ser. No. 12/399,965 entitled "OPEN AND COVERT DETECTION MECHANISMS FOR MATERIALS AT LOCATIONS OF INTEREST" filed on Mar. 8, 2009, copending U.S. patent application Ser. No. 12/399,967 entitled "OPEN AND COVERT DETECTION MECHANISMS FOR MATERIALS AT LOCATIONS OF INTEREST" filed on Mar. 8, 2009, and U.S. patent application Ser. No. 11/352,800 entitled "ILLUMINATION AND DETECTION ARCHITECTURE" filed Feb. 13, 2006, which claims the benefit of U.S. Provisional Patent Application Ser. No. 60/652,151 entitled "TARGET COMPOSITION DETECTION ARCHITECTURE" and filed Feb. 11, 2005. The entireties of the above-noted applications are incorporated by reference herein.

TECHNICAL FIELD

This invention is related to security systems at points of entry, chokepoints, or other desired locations for sensing/detecting the presence or absence of at least drugs and/or explosives, on persons, vehicles, ships, and aircraft, for example.

BACKGROUND

The security of any country is becoming threatened more and more by individuals who seek to impose their own beliefs on the society by destabilizing the current governments, taking retribution against others, and/or to profit illegally from sales of drugs and guns, for example. Accordingly, governments are devoting more resources to deter such efforts. Such individuals and products can enter a country by many different means, ranging from walking in as human carriers to other transportation means (e.g., vehicles and other craft) that transport large containers thereby making it very difficult to adequately process such containers, craft and vehicles in large numbers without having an economic impact.

Some such materials do need not be supplied or conveyed in large quantities in order to do damage or cause harm to life and property. For example, small quantities of nuclear and biological material can pose great risk to human health. Moreover, given the destructive power in economic terms as well as human life associated with such small amounts it seems that individuals are more apt to take the risk of dealing with these materials for personal gain or other reasons. Accordingly, airports and borders are being more closely monitored for individuals and the transport of illegal materials trying to enter (or leave) a country. However, the numbers of vehicles and people moving across borders is enormous. Similarly, the number of shipping containers being transported in and out of ports, and the number of large trucks hauling such containers provides an even more difficult task of ensuring that no harmful or illegal products or materials enter the country. In other words, the capability to quickly monitor, scan and detect each human, container, truck and ship, for example, without having a negligible effect on commerce and travel is nearly an impossible task.

Current methods include x-ray detection and other nuclear techniques for non-human examination, such as at airports for luggage, none of which address the possibility that such materials can be carried by the person. Similarly, such applications are not conducive to scanning people or for adequately processing large numbers of vehicles, large vehicles and large transport vessels, for example. Accordingly, a need exists for improved techniques, systems, and methodologies for detecting materials of interest in such environments.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The subject invention is a system for sensing drug, explosives, and/or other materials of interest at desired points or locations. For example, the invention can be employed in a wide variety of applications, including, but not limited to, checkpoints, embassy buildings, military entrances, government buildings, ports of entry, road checkpoints, chokepoints, public transportation, cargo transportation systems, or virtually any area that is desired to be scrutinized for the presence of certain chemical compositions and related components.

In another aspect thereof, the invention can be employed in a concealed or open implementation to facilitate the detection of desired chemical components (e.g., components related to explosives and/or drugs). The system is simplistic, cost effective, and can be easily concealed in floors, ceilings, walls, portable containers, and handheld units, for example.

The system includes an optical receiving and data communications architecture for sensing at least drugs and explosives. The system includes a fiber optic front end having a lens attached thereto that focuses and/or concentrates light reflected from a target into the fiber filament for communication to an optical sensor. When a target is illuminated at a predetermined wavelength, a vapor plume associated therewith is energized such that photoluminescent information is received into the fiber/lens pair. The photoluminescent information is communicated over a fiber communications network to a remote processing and analysis system for processing and analysis to determine its chemical components.

In support thereof, the invention disclosed and claimed herein, in one aspect thereof, comprises an optical receiving component that receives photoluminescent information representative of a chemical component of an illuminated target, the chemical component associated with at least one of a drug and an explosive material. The system further includes a communications component that communicates the photoluminescent information to a remote location for processing and analysis to determine the chemical component. In one implementation, the communications component is a fiber optic communications system that facilitates communication of the photoluminescent information to an optical sensor that captures the photoluminescent information in the form of an image. In another implementation, the communications component includes the fiber optic communications system and radar (e.g., phased array) that facilitates communication of a photoluminescent image to the optical sensor.

To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
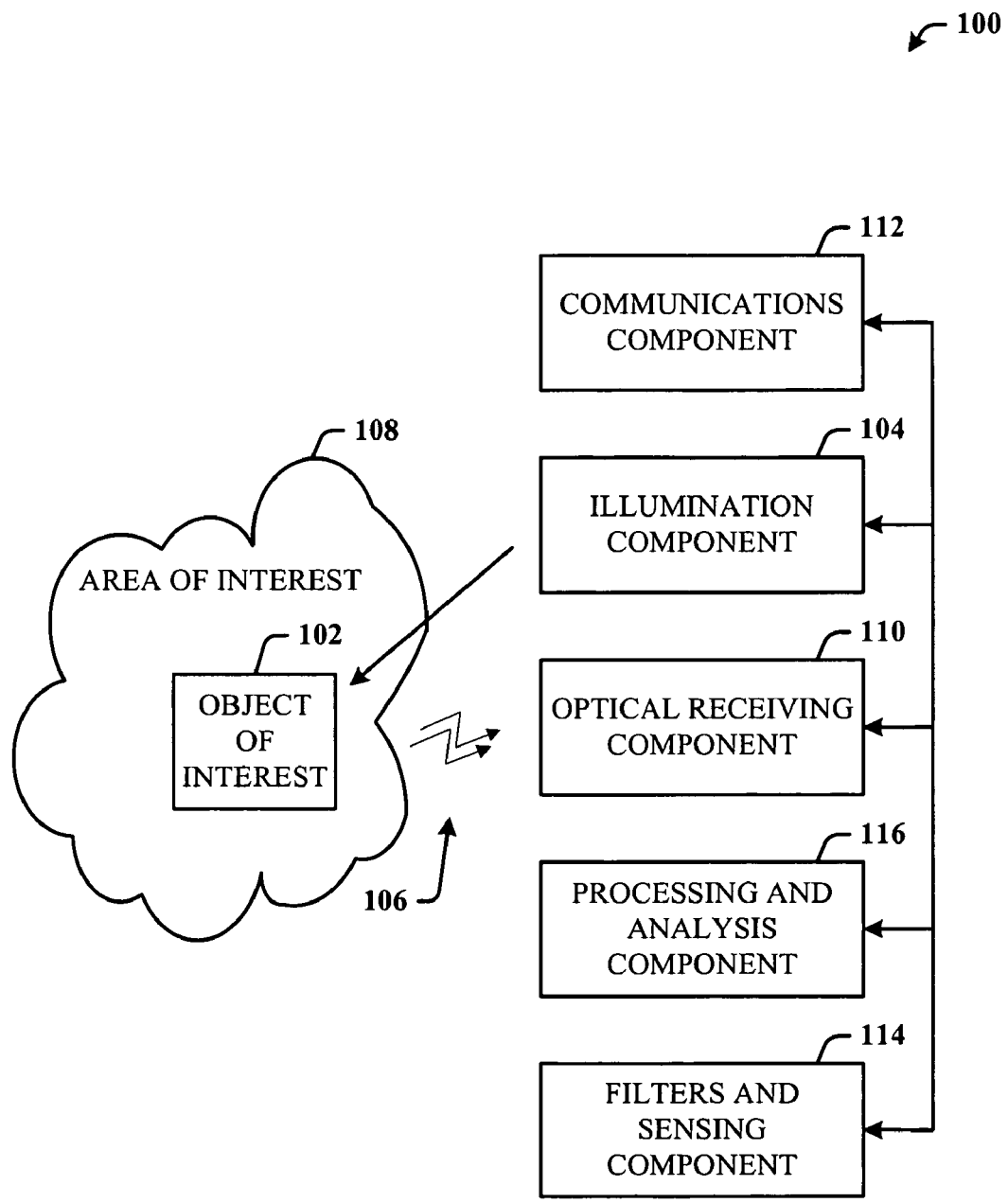
FIG. 1 illustrates a sensing and detection system for sensing and detecting materials of interest drugs and/or explosives in an area of interest in accordance with the subject invention.

The invention is now described with reference to the drawings, wherein like reference numerals are used to refer to like elements throughout. In the following description, for purposes of explanation, numerous specific details are set forth in order to provide a thorough understanding of the subject invention. It may be evident, however, that the invention can be practiced without these specific details. In other instances, well-known structures and devices are shown in block diagram form in order to facilitate describing the invention.

As used in this application, the terms "component" and "system" are intended to refer to a computer-related entity, either hardware, a combination of hardware and software, software, or software in execution. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

The disclosed architecture includes a system for sensing drug, explosives, and/or other materials at desired points or locations. For example, the architecture can be employed in a wide variety of applications, including, but not limited to, checkpoints, embassy buildings, military entrances, government buildings, ports of entry, road checkpoints, chokepoints, public transportation, or virtually any area that is desired to be scrutinized for the presence of certain chemical compositions and related components. The architecture is suitable for a concealed (covert) and/or open implementation to facilitate the detection of desired chemical components (e.g., components related to explosives and/or drugs). The system is simplistic, cost effective, and can be easily concealed in floors, ceilings, walls, portable containers, and handheld units, for example.

It is to be understood that the term "change" as used herein is intended to include any one or more of detectable events such as a chemical change, photoluminescent events such as fluorescence and phosphorescence, photofragmentation or photodisassociation, to name a few. The type of energy as well as characteristics and/or parameters of the energy are controlled to facilitate detecting the presence or absence of the selected material at the target by the corresponding presence or absence of the change (or change signals), as exhibited by detected photon signals when the light impinges on the target and/or particulate materials. For example, where the imposed energy is light, the frequency can be controlled to cause detectable changes in vapors at the target and/or particulates on the surface or slightly beneath the surface of the object.

Referring initially to the drawings, FIG. 1 illustrates a sensing and detection system 100 for sensing and detecting materials of interest (e.g., drugs and/or explosives) in an area of interest in accordance with the subject invention. An object of interest (or target) 102 is illuminated with a light source from an illumination component 104 such that vapors and/or particulates associated therewith are energized generating detectable change data 106 (e.g., photoluminescence) that represents a chemical component of a drug and/or explosive material. The object of interest 102 passes through an area of interest (or inspection area) 108 that is covertly and/or openly configured with an optical receiving component 110. The optical receiving component 110 can include a single fiber filament that receives the change data 106 and facilitates communication of the photons associated therewith to a communications component 112. Alternatively, the optical receiving component 110 can be a plurality of optical fibers positioned separately and/or in several bundles to receive the photon signals associated with the change data 106 and communicate the photon signals to the communications component 112.

The communications component 112 further conducts signals associated with the change data to a filters and sensing component 114 that filters the photons to allow only the desired wavelength(s), and an optical sensor that senses the received photons as, for example, an image. From there, the photon signals representative of the change data 106 are passed to a processing and analysis component 116 to detect the chemical(s) present in the vapors and/or particles associated with the object of interest 102.

It is to be appreciated that the distance from the optical receiving component 110 to the filters and sensing component 114 can be a short distance (on the order of centimeters and meters) or a much greater distance (on the order of 100's to 1000's of meters). In support there of, if the distance is short, optical fiber can be run from the target inspection area directly to the filters and sensing component 114 without the need for the communications component 112 (e.g., the need for optical repeaters, focusers, etc.). Alternatively, if the distance from the optical receiving component 110 to the filters and sensing component 114 is a much greater distance (on the order of 100's to 1000's of meters), various other means can be employed to ensure that the optical signals received from the change data are communicated to the filters and sensing component 114. For example, the communications component 112 can include further lengths of optical fibers, multipliers, repeaters, etc., in addition to wireless systems that can communicate image data (e.g., phased array radar).

In another implementation, the optical receiving component 106 can include fiber filaments, some or all having a lens attached thereto that assists in coupling more photons thereinto than if the lens were not present. This is described infra.

Figure 2:
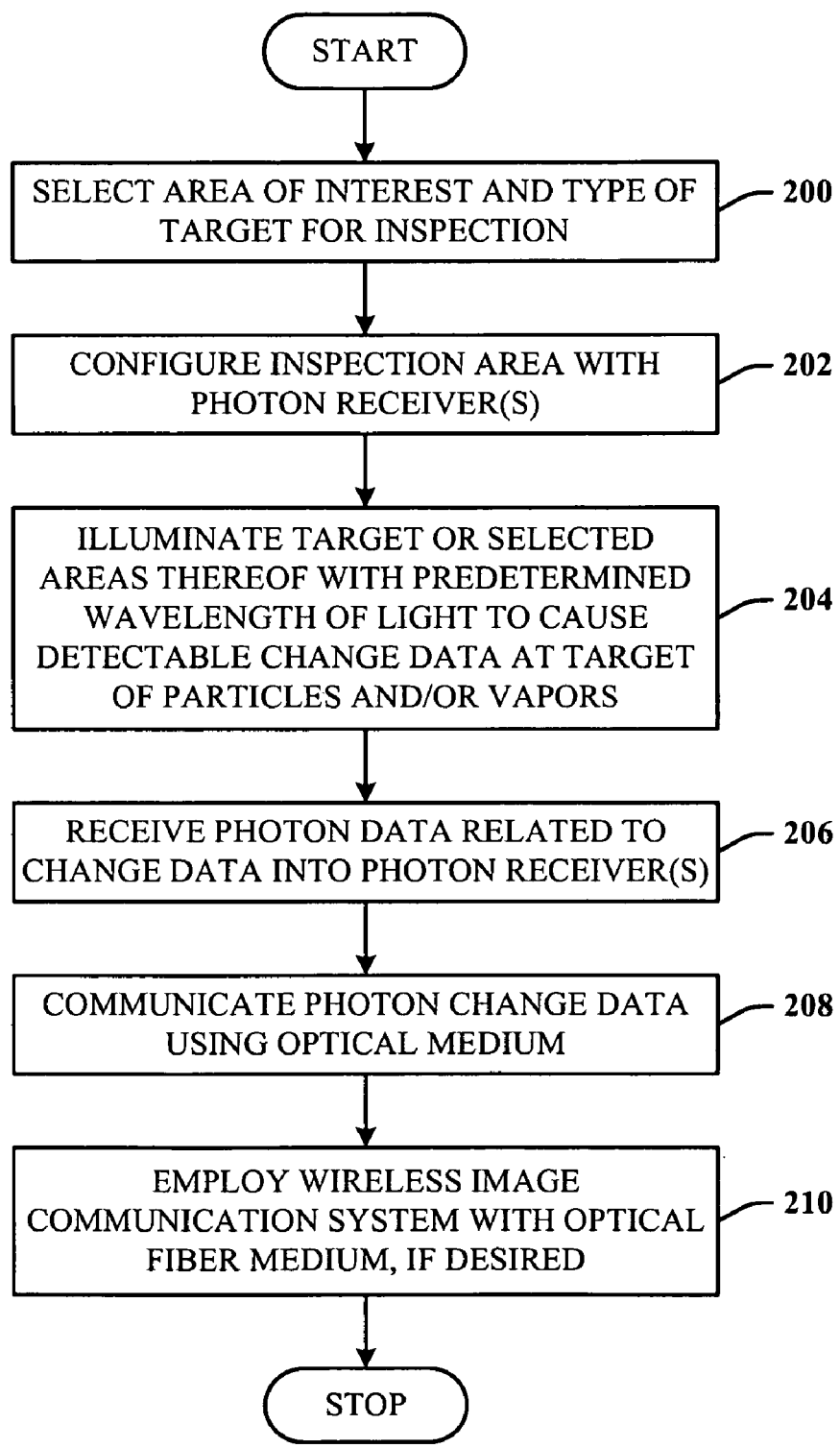
FIG. 2 illustrates a methodology of sensing and detecting materials in an area of interest in accordance with the subject invention.

FIG. 2 illustrates a methodology of sensing and detecting materials in an area of interest in accordance with the subject invention. While, for purposes of simplicity of explanation, the one or more methodologies shown herein, e.g., in the form of a flow chart, are shown and described as a series of acts, it is to be understood and appreciated that the subject invention is not limited by the order of acts, as some acts may, in accordance with the invention, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the invention.

At 200, an area of interest (e.g., building ingress/egress, shipping port, . . . ) is selected as well as the type of target (or object of interest) for inspection. At 202, an inspection area is configured with one or more photon receivers (e.g., optical fiber filaments). At 204, the target is illuminated, or selected areas thereof, with a predetermined wavelength of light to cause detectable change data (e.g., photoluminescence) on or near the target vapors and/or particulates. At 206, the photon signals representative of the change data is coupled into the fiber filament(s). At 208, the photon change data is communicated through the fiber filaments. At 210, where greater distances are required, a wireless image communications systems can be employed with the fiber medium, if desired.

Figure 3:
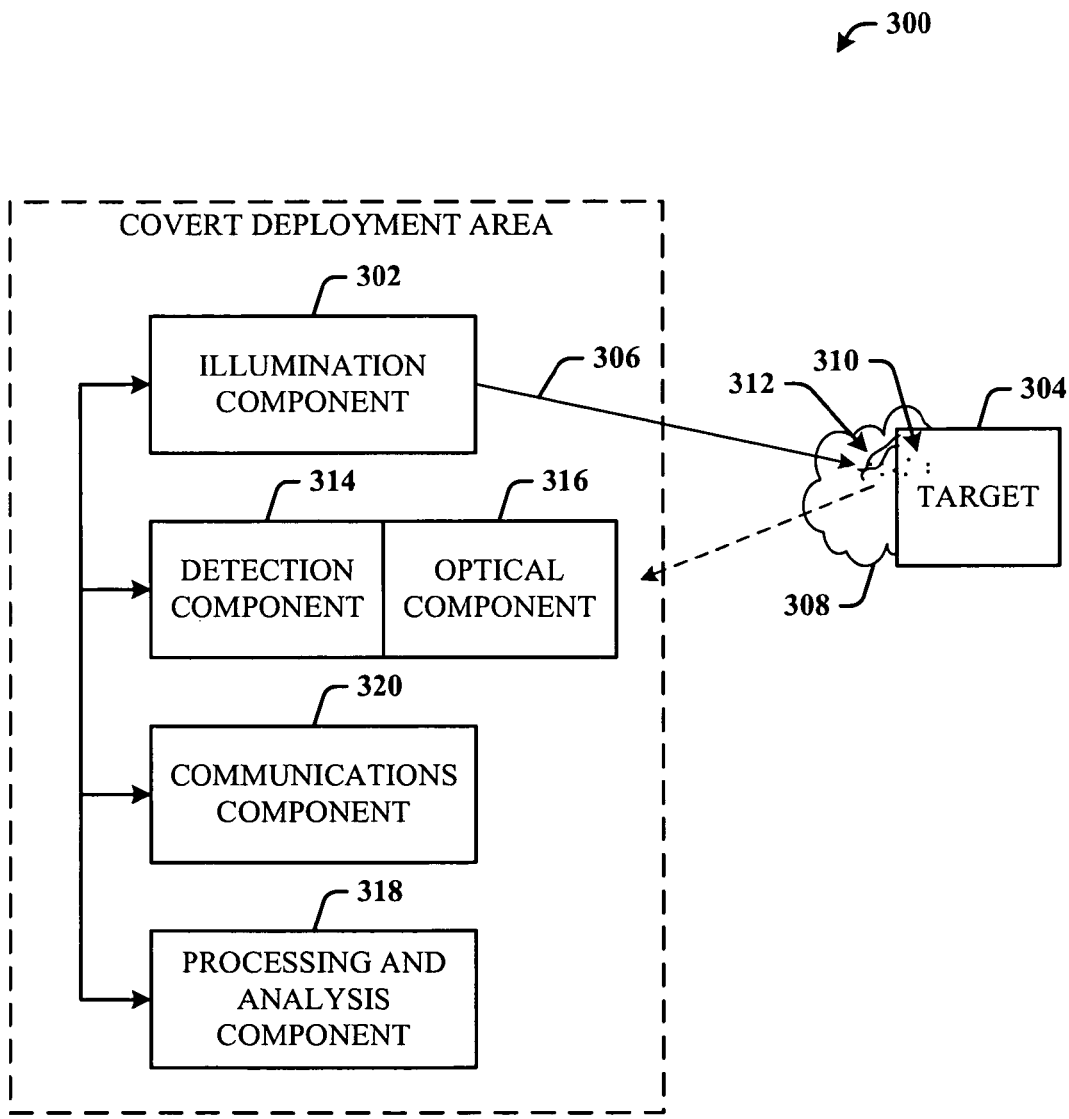
FIG. 3 illustrates a system that facilitates chemical component detection in accordance with the subject invention.

FIG. 3 illustrates a system 300 that facilitates change detection and processing in accordance with the subject invention. The system 300 includes an illumination component 302 that illuminates all or a portion of a target 304 with light 306 at a predetermined wavelength. The target 304 can exhaust a vapor 308 that includes a chemical component associated with the composition of the target 304 and/or its contents. Alternatively, or in combination therewith, the target 304 can have associated particulate matter 310 which reacts to the light 306 such that a detectable change 312 is made to occur. The wavelength of the light 306 as controlled and directed to the target area is designed to interact with a particular chemical present in the vapor plume 308 and/or particulates 310 such that if the chemical is present, the change 312 occurs in the vapor plume 308 that is detectable.

In support thereof, the system 300 further includes an optical component 316 that interfaces to couple photon signals representative of the change information 312 to a detection component 314. In one implementation, the detection component 314 interfaces to an optical component 316 which includes a fiber filament (not shown) that conducts the change information 312 to the detection component 314. Either (or both) of the optical component 316 or (and) the detection component 314 can further include the hardware and/or software desired to preprocess the change information 312, and provide further photon filtering, including one or more photon sensors, for example.

The detection component 314 outputs detection data to a processing and analysis component 318 that further can perform analysis thereof. For example, it is to be appreciated that many different types of analysis can be conducted such as image analysis, color analysis, timing analysis, signal conditioning from the detection component 314, etc. The processing and analysis component 318 can also function as a central monitor and control system for the system 300 that controls the illumination component 302 to tune the accompanying light source to the desired frequency, orientate the light source in a desired direction, conduct onboard tests, manages power subsystems on/off or in reduced power modes, for example, and generally, manage subsystems of the illumination component 302 for all purposes.

The system 300 also includes a communications component 320 that facilitates wired and/or wireless communications between the system 300 and a remote system (not shown), and between any of the system components (302, 314, and 318). Additionally, the communications component 320 can also be employed to communicate the detection data from the detection component 314 to suitable remote system for further processing. As indicated, the system 300 can be deployed covertly such that the target is not aware of the illumination component 302, detection component 314, optical component 316, processing and analysis component 318 and communications component 320.

Figure 4:
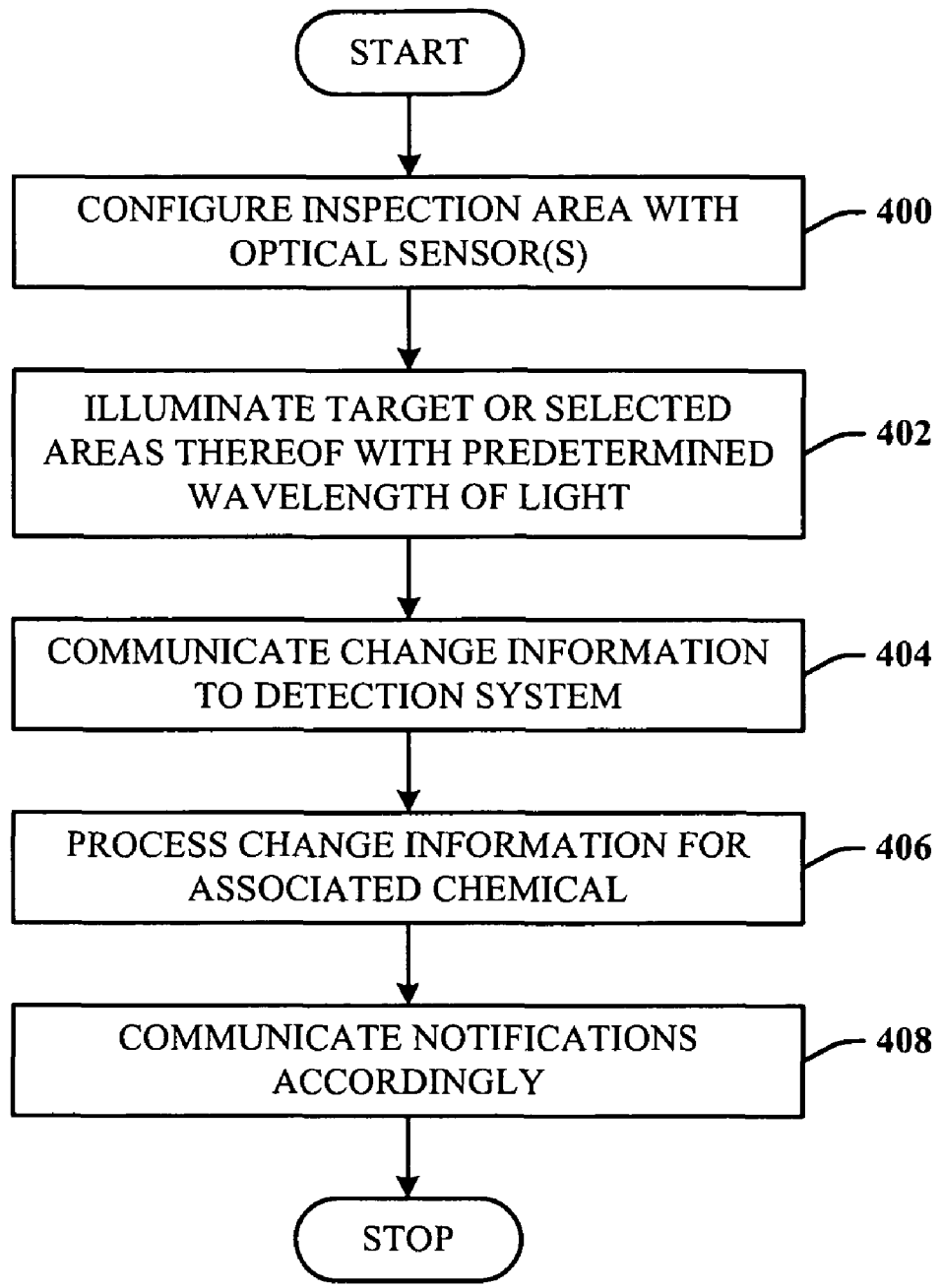
FIG. 4 illustrates a methodology of inspecting an area for selected chemicals in accordance with the invention.

FIG. 4 illustrates a methodology of inspecting an area for selected chemicals and/or materials and communicating alerts or notifications, in accordance with the invention. At 400, the inspection area is configured with at detection system that includes one or more optical sensors that receive and process optical data. At 402, a target passes through the inspection area, and the target or portions thereof are illuminated with light of a predetermined wavelength that energizes certain chemicals present in a vapor plume and/or associated with particulates associated with the target. Alternatively, the target can be stationary, and the inspection system is moved past the target, scanning the target with the light to detect the change data. If one or more of the selected chemicals are present in the vapor plume and/or particulates, a change occurs that is detectable. At 404, change information associated with the change is communicated to a detection system. The means for communicating the change information can be via optical means and/or phased array radar, or any other suitable means, for example. At 406, the detection system, in cooperation with other subsystems, facilitates the processing and analysis of the change information to determine if the change information is associated with chemicals or materials desired to be detected. If so, at 408, one or more notifications are processed to alert other systems or users of the detected chemical component and/or particulate material.

For explosive residue, chemical compounds of interest can include trinitrotoluene (TNT), dinitrotoluene (DNT), octahydro-1,3,5,7-tetranitro-1,3,5,7-tetrazocine (HMX), and hexahydro-1,3,5-trinitro-1,3,5-triazine (RDX), for example. The subject architecture can illuminate and detect "nitrate explosive mixtures", which is intended to be an all-encompassing term, including all forms of sodium, potassium, barium, calcium, and strontium nitrate explosive mixtures.

It is to be appreciated that the subject invention is not limited to detecting explosives and/or drugs on humans, vehicles, airplanes, ships, etc., but can also be employed to detect such chemical components in soil. Explosive molecules are semi-volatile organic compounds. Explosive compounds, or their degradation products, used in military and industrial applications, and therefore are present in soil where explosives, landmines and unexploded ordnance (UXO) are present or where explosion events have occurred to directly contaminate the soil with explosive compounds. These include, but are not limited to, $C_4H_8N_8O_8$ or HMX, $C_3H_6N_6O_6$ or RDX, 1,3,5-trinitrobenzene ($C_6H_3N_3O_6$ or TNB), 1,3-dinitrobenzene ($C_6H_4N_2O_4$ or DNB), methyl-2,4,6-trinitrophenylnitramine ($C_7H_5N_5O_8$ or Tetryl), nitrobenzene ($C_6H_5NO_2$ or NB), 2,4,6-trinitrotoluene ($C_7H_5N_3O_6$ or TNT), 2,4-dinitrotoluene ($C_7H_6N_2O_4$ or 24DNT), 2,6-dinitrotoluene ($C_7H_6N_2O_4$ or 26DNT), o-nitrotoluene ($C_7H_7NO_2$ or 2NT), m-nitrotoluene ($C_7H_7NO_2$ or 3NT), p-nitrotoluene ($C_7H_7NO_2$ or 4NT), nitroglycerin ($C_3H_5N_3O_9$ or NG), 4-amino-2,6-dinitrotoluene ($C_7H_7N_3O_4$ or 4-Am-DNT), 2-amino-4,6-dinitrotoluene ($C_7H_7N_3O_4$ or 2-Am-DNT), and pentaerythritol tetranitrate ($C_5H_8N_4O_{12}$ or PETN).

Figure 5:
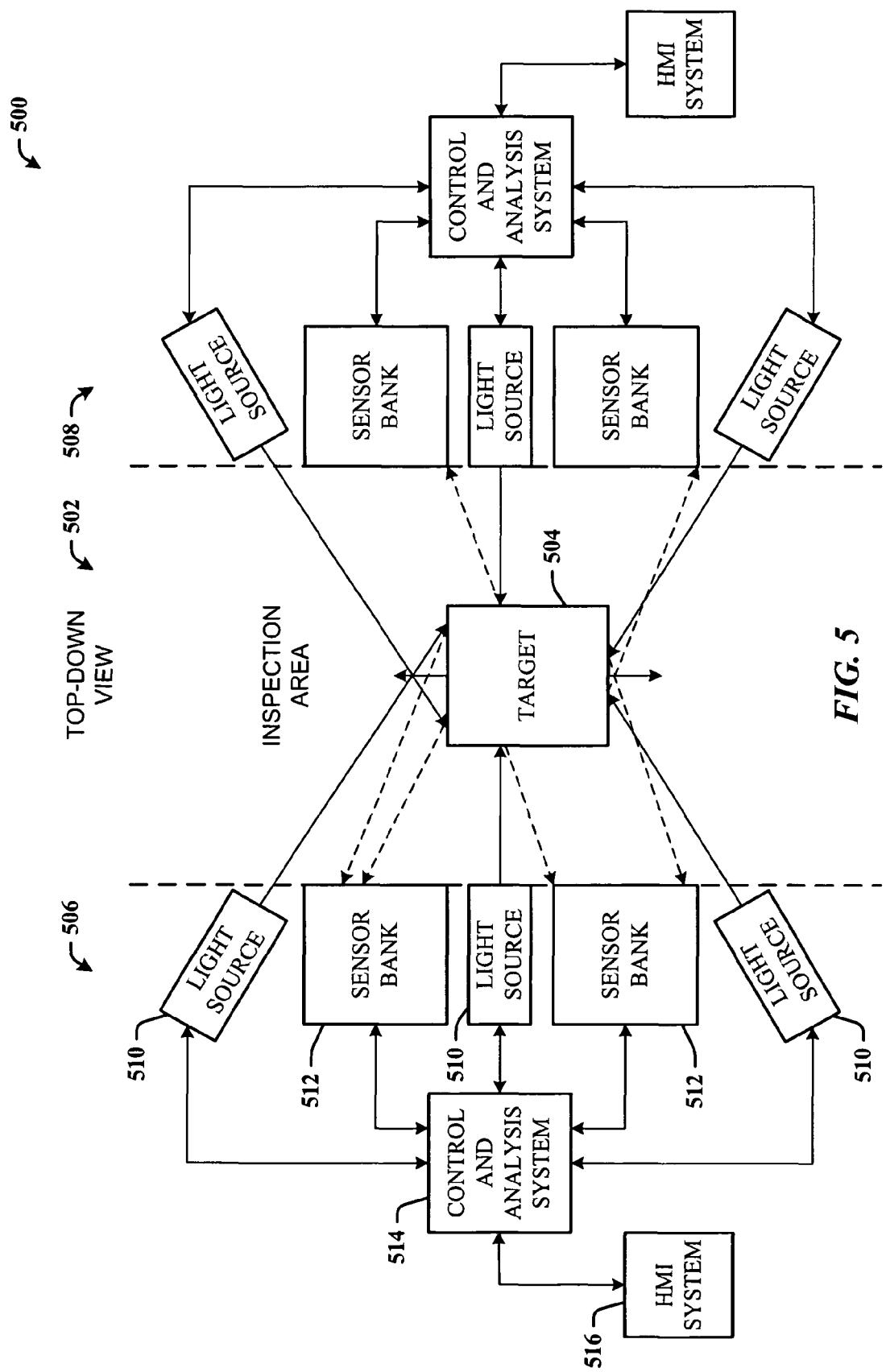
FIG. 5 illustrates a top-down view of an exemplary application of a detection system in accordance with the invention.

Referring now to FIG. 5, there is illustrated a top-down view of an exemplary application of a detection system 500 in accordance with the invention. The system 500 can be employed in a wide variety of applications, including, but not limited to, checkpoints, embassy buildings, military entrances, government buildings, ports of entry, road checkpoints, chokepoints, or virtually any area that is desired to be scrutinized for the presence of certain chemical compositions and components (e.g., explosives and/or drugs). In this exemplary implementation, the system 500 includes an inspection area 502 through which a target 504 is expected to pass. The inspection area 502 can be a canal (for ships or other water craft), an airport area where planes are expected to pass, a doorway of the plane, a doorway to or from a building, a drive entrance into a compound area through which vehicles must pass, and so on. The locations and configurations in which the subject invention can be employed are substantially unlimited.

The system 500 depicts essentially two identical detection systems; a first system 506 and a second system 508. However, it is to be appreciated that only a single system can be employed or more than two systems. This is based on the type of coverage desired for a given application. For example, it may not be desired or required in one application to inspect under the target 504, but only on the sides. In another scenario it may be required to inspect one or more of the top, bottom, front, back, and both sides of the target 504, or small openings thereof. For example, a small opening can be ported to the outside of the container such that gases can be sampled or scanned for presence of the desired chemical and/or materials.

The first system 506 includes one or more light sources 510 that illuminate the target 504 or selected areas or portions thereof as the target passes by. Again, as described herein, it is also possible that the first system is mobile such that it moves along a stationary target. In one implementation, the first system 506 or portions thereof orbits above the target 504 to provide substantial scanning coverage of the target from above. One or more sensor banks 512 function to detect change information generated as a result of the light of the light source(s) 510 energizing chemicals in a vapor and/or particulate materials associated with the target 504, as described supra.

The sensor banks 512 can be bundles of optical fiber filaments packaged to sense and conduct the phonon signals associated with the change information as one or more images to a control and analysis system 514. The control and analysis system 514 includes the necessary hardware and/or software to process the received images or photon signals in order to determine if the images represent the chemicals desired to be detected (e.g., explosives and/or drugs). The first system 506 also includes an HMI (human-machine interface) system 516 connected to the control and analysis system 514 that facilitates human interaction therewith (e.g., viewing data, initiating commands, receiving data, . . . ).

In this example, the second system 508 can be configured like the first system 506. However, it need not be. Moreover, there may not be a requirement for the second system 508 at all.

In that there are multiple light sources 510 such that different areas of the target 504 can be processed for the desired chemical component or material, the sensor banks 512 can obtain multiple change information images that are different. Thus, images from a single perspective (e.g., from only the top light source) can be processed on a "per channel" basis. This is because it is possible that more than one type of chemical component or material on a list of target chemicals can be detected and will be processed. In support thereof, the control and analysis system 514 can include multi-channel image processing capability that processes each channel of images over multiple "frames" and reacts accordingly to the detected results.

In this example, it is shown that when the light sources 510 of the first system 506 energize the target vapor and/or particulates, such change information is detected by the second system 508. However, this is not required, in that the first system 506 (or the second system 508) is capable of illuminating and detecting the change information without the second system 508 (or the first system 506) being in place. It is also to be appreciated that the first and second systems (506 and 508) can be interconnected by a wired and/or wireless technology.

In many cases, it will be advantageous in a particular application for the target 504 not to know that it is being inspected. In this scenario, the first and second systems (506 and 508) can be concealed in a structure proximate to the inspection area 502. In that the light sources 510 can be lasers and the sensor banks 512 the ends of optical fiber, concealment is made significantly easy. Moreover, utilization of such system components (lasers and fibers) further promotes the implementation of smaller more mobile detection systems (e.g., hand carry systems).

The control and analysis system (CAS) 514 can include an imaging component for image detection and processing of a detectable change at a target 504. The imaging component receives target information related to a detectable change at the target 504 as a result of being illuminated by the illumination source 510.

The CAS 514 can include subsystems that facilitate initialization (and/or self calibration) and baseline processing for eliminating effects of ambient conditions, for example. In support thereof, the CAS 514 can include an imager subsystem for receiving the target information as photons that are filtered through a photon filter to remove unwanted signals. The CAS 514 can also include a baseline processing control component that facilitates initialization and/or calibration of the imager subsystem prior to capturing a reading of the target information. For example, it is desired to eliminate the effects of the ambient lighting conditions by first capturing the ambient or background lighting data for eventual subtraction or elimination from the final image data. Next, capture of the working conditions can be recorded by briefly imposing illumination on the target 504 with the illumination source 510, and then capturing an image so as to process the illuminated target data against the ambient lighting conditions to obtain a delta value.

The imaging component of the CAS 514 can also include a shutter (or baffle) control component that closes off substantially all light to the imager elements to allow any residual readings (or photon activity) on the active elements of the imager to subside or bleed off. It is to be appreciated that such shutter can be opened and closed in short periods of time (e.g., milliseconds) in support of making the initialization process very short in terms of time. This will be controlled to reach the desired "black" criteria or residual photon activity on the imager before initiating the next image capture.

Once the ambient lighting conditions, affects of illumination on the target, and residual imager conditions have been measured and accounted for, detection of the desired material of interest at the target can commence. Accordingly, when the illumination is imposed on the target 504, the imager subsystem receives back photon information from the target 504 via the sensor banks 512 related to the ambient lighting conditions and the light on target impact, which are then processed and subtracted out. What remains should be any change information recorded in the snapshot or image as captured by the imager. It is to be appreciated that this process can be performed many times in a very short period of time, thereby receiving large amounts of data which can be processed to confirm or deny or provide a likelihood of the presence or absence of the material of interest. Such processing can be provided by an imager software processing component. This processing component can include high speed processing hardware (e.g., digital signal processors) and/or software for the rapid analysis, processing, and turnaround of imaging data in order to obtain results.

The illumination source 510 can also include a positioning control component (e.g., a servo control device) for controlling the direction of illumination to the target 504. Accordingly, the illumination (e.g., a beam from a laser) can be finely controlled to impact the target 504.

The CAS 514 can also, optionally, include a range finder component for determining an approximate distance-to-target value. This distance value can be used to control the illumination on the target 504. For example, if the distance value exceeds a predetermined minimum distance value, it will be understood that some adjustment to the illumination beam may be required, for example, related to focus or dispersion thereof. On the other hand, if the distance value is less than the minimum value, the beam may not require further adjustment prior to examining the target for the material of interest. Range determination can be accomplished by several different techniques, such as laser detection and/or high frequency sonic means, for example.

The CAS 514 of the system 500 can also include a system software processing and control component for process and control of any of the aforementioned components. In particular, if the range finder component returns a value which indicates that the illumination source 510 requires adjustment, the process and control component can interface to the positioning control component to achieve the desired adjustment in the illumination beam, with respect to at least the amount of dispersion and placing the beam on the target 504.

In another implementation, multiple light beams of different wavelengths, one for each material of interest, are emitted onto the target 504. This allows multiple different materials of interest to be detected substantially simultaneously. Accordingly, in this particular application, both drugs and explosives could be scanned for. Similarly, the target 504 can be scanned for two different kinds of explosives.

The additional system 508 can also work as a backup system should the first system 506 need to be taken offline for repairs or troubleshooting, for example. Alternatively, the second system 508 can be a secondary system that simply provides corroborating data for the first (or primary) system 506. In yet another implementation, the first and second systems (506 and 508) can work in an interleaved fashion where the first system 506 takes a first scan of the target 504, and then the second system 508 scans the target 504 while the first system processes the first scan data, followed by now the first system 506, and so on. The interleaved implementation is more suitable for high speed sensing applications.

Figure 6:
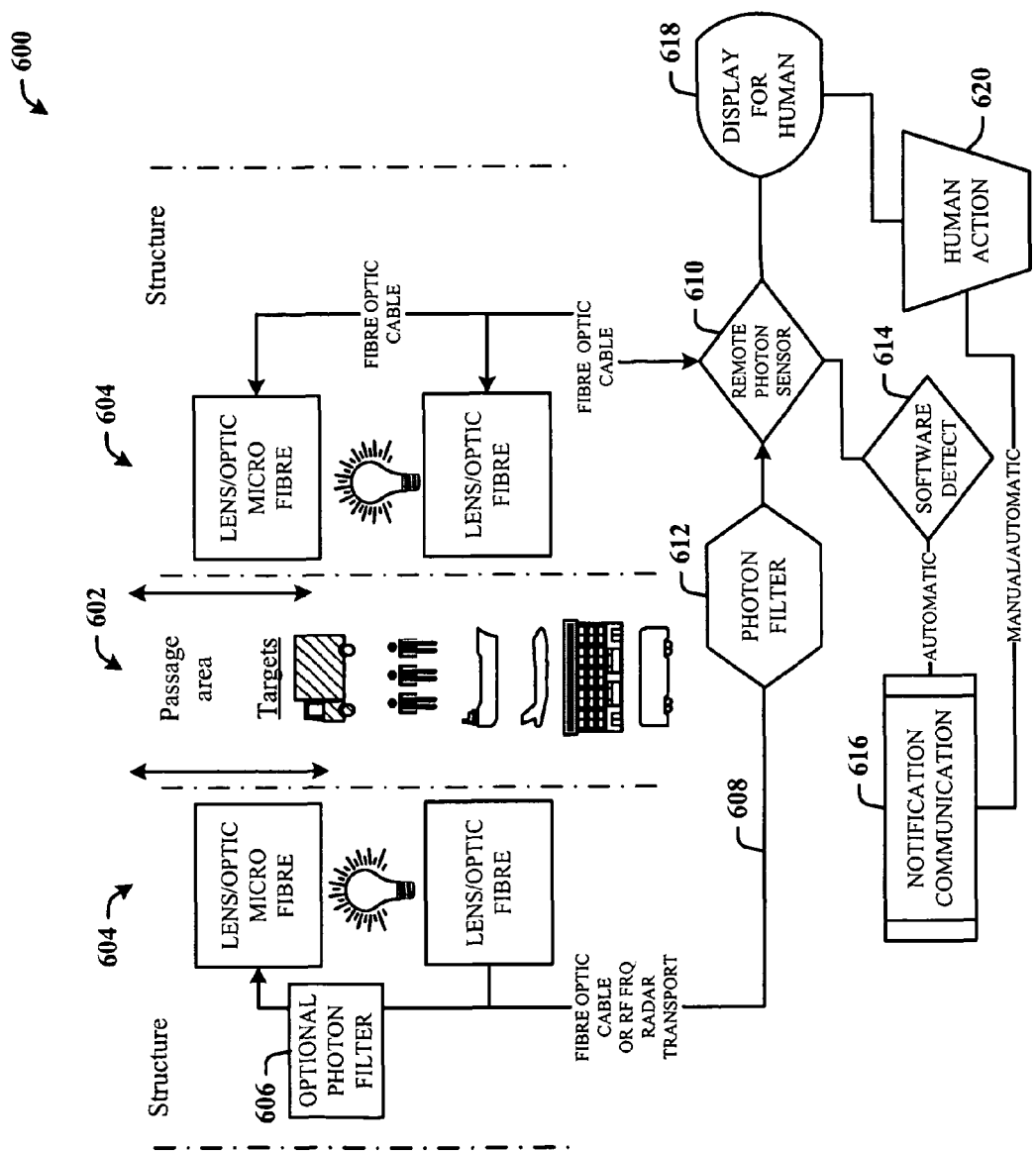
FIG. 6 illustrates a more detailed detection and analysis system for sensing materials of interest in a transportation system in accordance with the invention.

FIG. 6 illustrates a more detailed detection and analysis system 600 for sensing materials of interest in a transportation system in accordance with the invention. The system 600 can be concealed in any structure such as walls, hulls, mobile barriers, and doors, for example, with sensors being in the structure, on the surface and/or the outside of the structure. Alternatively or in combination therewith, the system 600 can be open for detecting explosives, drugs and/or other desirable materials, and other chemicals normally associated with explosives and/or drugs. In this embodiment, a passage area 602 is instrumented that is associated with a variety of different scenarios, for example, trucks, humans, animals, ships, airplanes, buses and buildings. Thus, the subject architecture can be employed at areas such as checkpoints, embassies, buildings, military entrances, public and commercial transports, warships, military vehicles, private and government buildings, border inspection areas, internal and external vehicle detection, transportation containers, ports of entry, roads, chokepoints, and many more locations and applications.

The system 600 employs optical fiber and/or optical fiber with lens attached as sensing means, and which is described infra. For example, on either side of the passage area 602, lens/optical fiber subsystems 604 can be deployed for receiving photon signals representative of change data caused to occur when light sources (represented by light bulbs, actually or symbolically) impose light on targets moved or passed therethrough. Where incandescent light sources are employed, a special coating on the bulb can facilitate emitting light at the desired wavelength to expose suitable change data (not shown).

The fiber/lens systems 604 can be optionally filtered with photon filters 606 prior to optical transmission of the detected change information over fibers 608 to a sensor system 610 via a photon filter subsystem 612. Transmission can be directly via optical fiber cables 608, by wireless radar for image transmission, and other suitable means for the given application. The fiber/lens and illumination systems can be embedded into structures for optimum concealment. Such structure can include, for example, walls, hulls, mobile barriers, doors, and so on. Moreover, multiple illumination sources can be employed. The illumination source can also be activated, modulated and/or continuous, for example.

Additionally, other systems can be utilized in conjunction with the sensing/detection systems, including a processing and analysis system represented by a software detect block 614, a notifications system 616 that interfaces automatically to the software detection system 614, user interface systems such as a display system 618 and human interaction block 620, and the like.

In one implementation, the system 600 can detect trace explosives and/or drugs at a distance that ranges from about 15 feet to about 25 feet. In another implementation, the system 600 detects trace amounts at a distance that ranges from about 50 feet to about 500 feet. In yet another implementation, the system 600 can detect trace amounts of explosives and/or drugs at a distance that ranges from about 500 feet to about 5000 feet.

Figure 7:
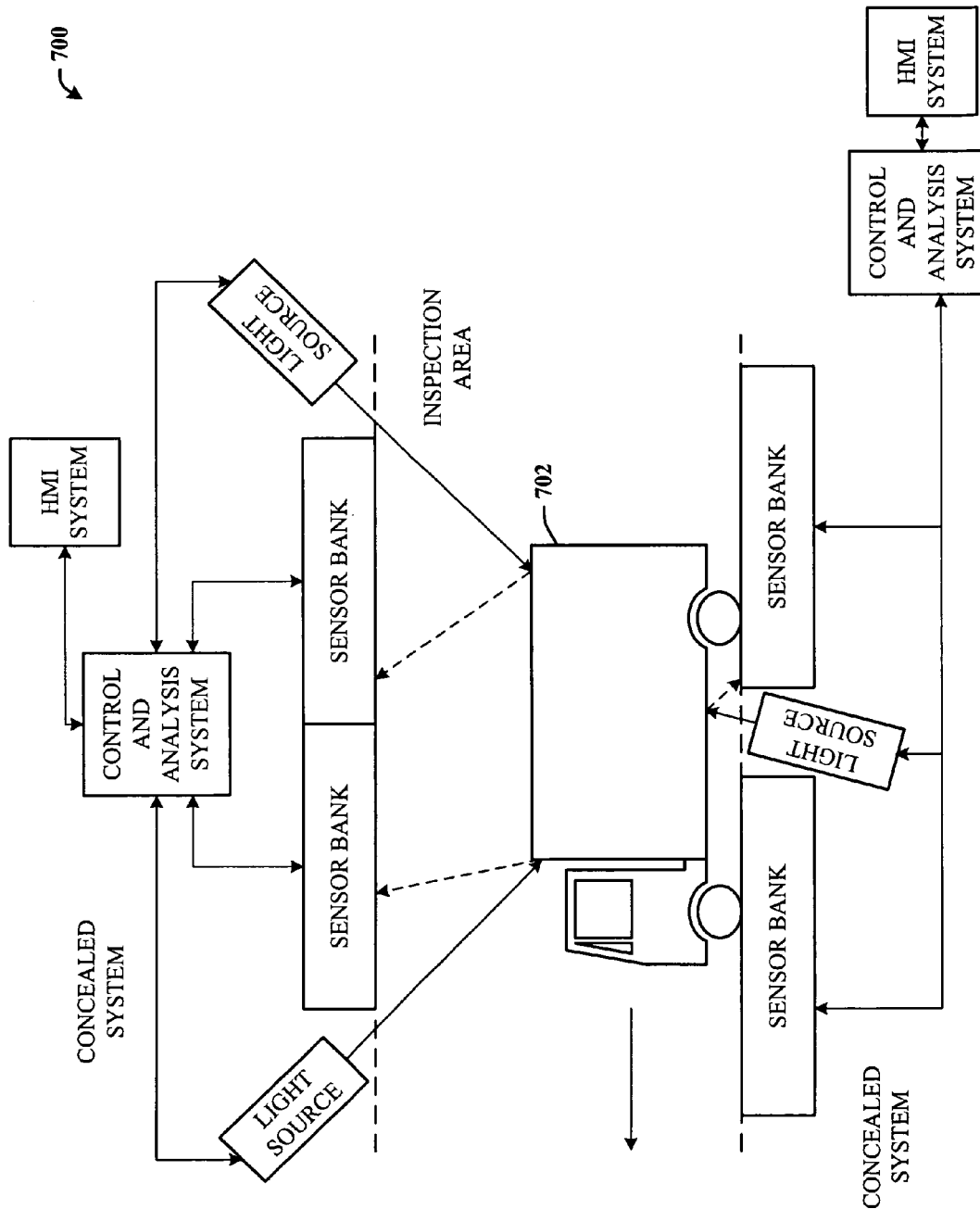
FIG. 7 illustrates a side-view of a concealed vehicle detection and analysis system in accordance with the invention.

FIG. 7 illustrates a side-view of a concealed vehicle detection and analysis system 700 in accordance with the invention. In this particular implementation, the system 700 includes light sources and sensor banks both above and below (in the ground or structure foundation) a vehicle 702 that is passing though an inspection area. In one implementation, the system 700 can detect trace explosives and/or drugs at a distance that ranges from about 15 feet to about 25 feet. In another implementation, the system 700 detects trace amounts at a distance that ranges from about 5 feet to about 50 feet. In yet another implementation, the system 700 can detect trace explosives and/or drugs at a distance that ranges from about 0 feet to about 100 feet.

The inspection area can be designed to force the target through the area such that inspection is successful. For example, if the vehicle is an automobile, the vehicle can be routed through an area that forces the vehicle over and under the appropriate illumination and sensors. Similarly, if the vehicle is a midsize truck, the vehicle can be routed through tracks, for example, that force or guide the vehicle over/under the appropriate inspection systems. It is also to be appreciated that the speed of the object of interest in inconsequential, since the change can be detected substantially instantaneously by the inspection system. This is particularly advantageous where vehicle traffic is not to be significantly impeded.

Figure 8:
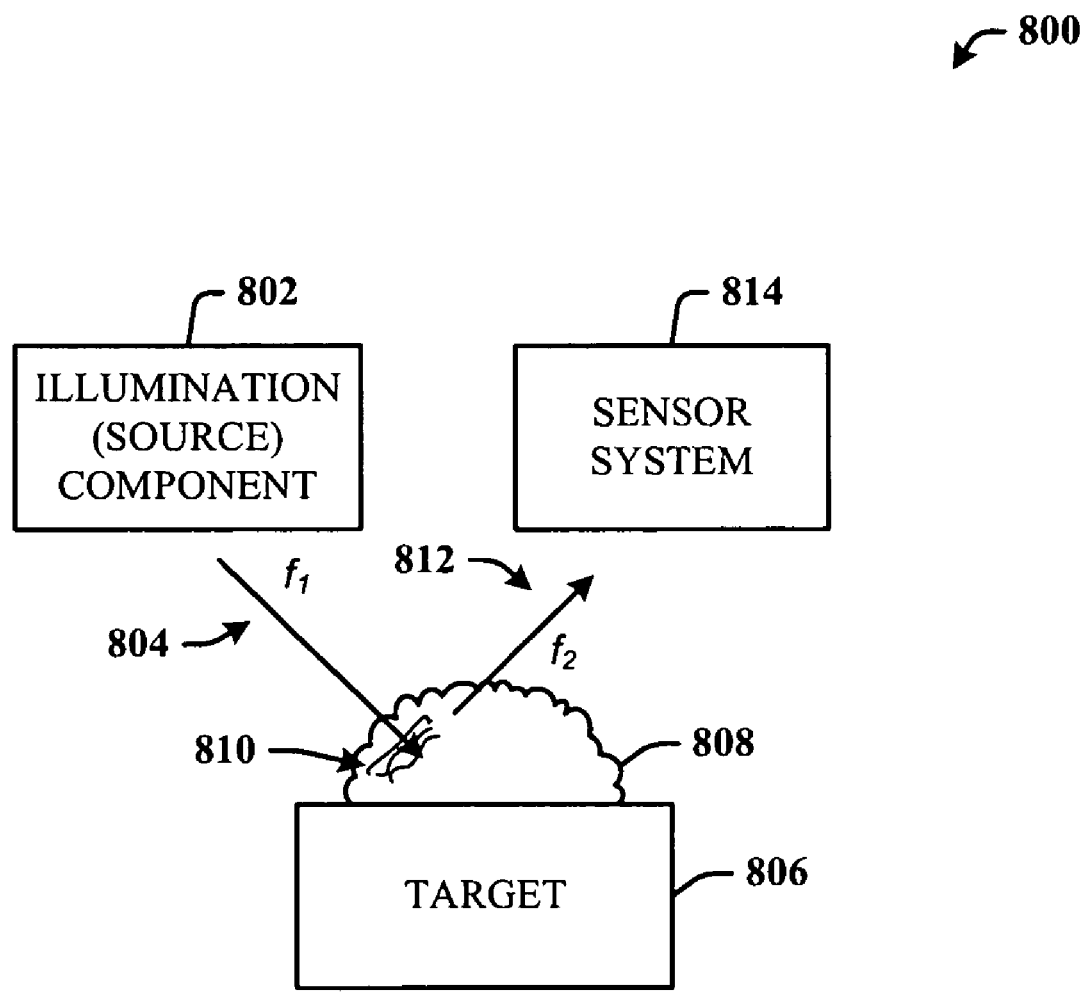
FIG. 8 illustrates a system that facilitates illumination and detection of one or more materials of a target in accordance with the subject invention.

Referring now to FIG. 8, there is illustrated a system 800 that facilitates the illumination and detection of one or more materials of a target via an associated vapor plume (or material outgassing) in accordance with the subject invention. The system 800 includes an illumination component 802 that provides a source of electromagnetic radiation (or energy) 804 (herein, also referred to as "light") that can be directed onto a target 806. The radiation 804 can be of a frequency that is visible or not visible to the human eye. For example, the illumination component 802 can be a LASER (Light Amplification of Stimulated Emission of Radiation—hereinafter, "laser"), which facilitates directing a visible coherent source of light onto the target 806. The illumination component 804 can also or alternatively be incandescent (with proper coatings to provide the suitable wavelength), for example, insofar as the light imposed causes a detectable change in the vapor 808 and/or particulate material associated with the chemical desired to be detected at the target 806.

The chemical composition of many types of materials, whether natural or manmade, is such that the objects that include such materials, and continually or periodically emit (or outgas) one or more gasses or vapors associated with the materials. Thus, there is the invisible vapor cloud 808 that exists in some volume of space proximate the target 806 and that includes chemical vapors associated with one or more types of materials in, on, and/or around the target 806.

In the example of FIG. 8, the vapor cloud 808 is shown to one side of the target 806, where the target 806 is a 3-D object, as opposed to the target 806 being an area or surface; however, in 3-D space, the vapor plume 808 can be on some or all sides of the target 806. It is to be appreciated that the target 806 to be illuminated and detected can be in the form of dust, a liquid or minute particles, again, which include and/or emit vapors proximately. For example, where a surface has been exposed or contacted by an object, perhaps by the object being placed on the surface and then removed, residual dust and/or smear of liquid, oil, etc., can exist on the surface that includes chemicals which when illuminated as the desired wavelength, can be detected. Alternatively, particulate matter can exist on and/or in that surface cracks such that the imposed light causes the particulate matter to exhibit the detectable change. In one example, the surface can be the surface of the earth (also referred to herein as "ground") such that if the target dust particles, for example, drifted to the ground, again, such minute chemical vapors associated with the dust particles exist for illumination and detection in accordance with the detection system 800.

In operation, the illumination component 802 imposes the light 804 at a predetermined frequency $f_1$ (or frequency range $f_1$-$f_r$) on the target 806, and when doing so, impacts the vapors 808 and/or particulate matter (no shown). The energy of the light 804 interacts with a certain chemical or chemicals in the vapor plume causing a brief change 810 in the vapors 808 (or portions thereof) that is detectable as a different frequency $f_2$ (or frequency range $f_1$-$f_d$) of detectable light 812 by a detector sensor system 814 that includes one or more sensors and associated processing capability suitable for detecting the desired chemical in a vapor or particulate material energized by the illumination component 802. The change 810 occurs and is detectable only as long as the light (or energy) 804 is imposed on the vapors 808 of the target 806 (or area) at the desired frequency (or wavelength). Thus, once the light 804 is removed from the target 806, the vapor change 810 reverts back to its original state, and hence, is no longer detectable by the detector sensor system 814.

Where the illumination component 802 includes a laser, the laser can be tunable, such that a predetermined frequency of light is output. Thus, laser-induced fluorescence (LIF) can be employed to cause the atmospheric vapor and/or target itself to exhibit certain properties that are detectable by the detector sensor system 814. As will be described infra, all that is required is that the target or gases/particulates associated with the target be illuminated and the change detected.

The system 800 is particularly suited for detecting drugs and/or explosives from near and/or distant locations. For example, in one implementation, trace amounts of nitrocompounds in the atmosphere or on surfaces can be detected, for example, compounds related to DMNA (N,N-dimethylnitrosamine), nitromethane, nitrobenzene, TNT, and RDX (Cyclotrimethylenetrinitramine) or RDX compositions, to name just a few.

It is to be appreciated that the illumination component 802 and the detector sensor system 814 can be interconnected such that the components (802 and 814) are controlled by a central control system. In another implementation, the components (802 and 814) are housed in a common chassis that is portable. In yet another implementation, the components (802 and 814) are integrated into a handheld portable chassis for use by a single user.

Figure 9:
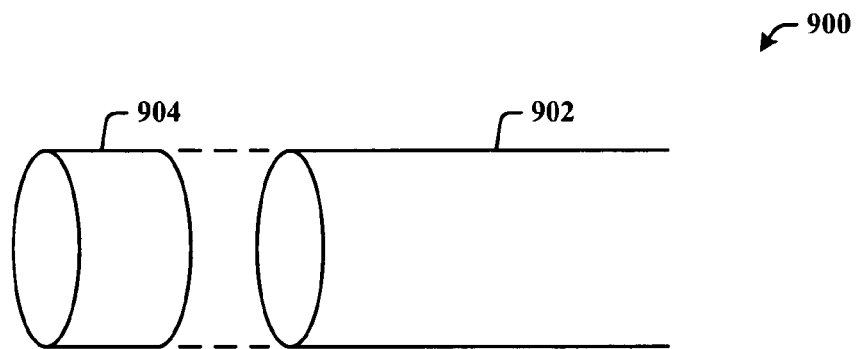
FIG. 9 illustrates an exemplary fiber sensing system in accordance with the invention.

FIG. 9 illustrates an exemplary fiber sensing system 900 in accordance with an aspect of the innovation. A fiber 902 includes a lens 904 attached to an end. Light from the end of a bare fiber can be highly divergent, and substantial power is lost in the fiber optic component unless a lens is used to improve collimation of the beam. The lens 904 can be a convex lens, a bi-convex lens, and a positive meniscus lens, for example, or any other lens suitable for capturing photon signals associated with the change information.

Figure 10:
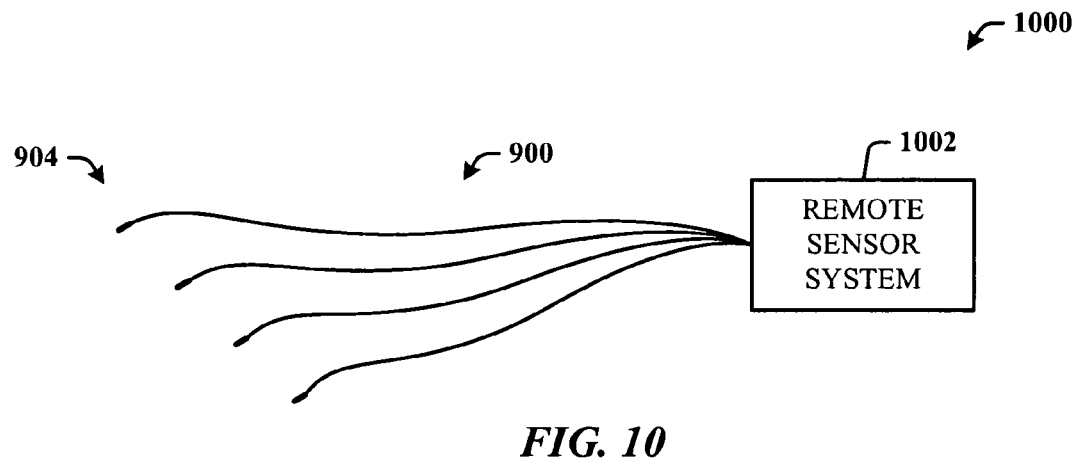
FIG. 10 illustrates a portable detection system of the subject invention.

FIG. 10 illustrates an exemplary system 1000 that employs multiple optical fibers 900 as sensing means for capturing the change information associated with target illumination described supra. Here, no intermediate communications components are required to transmit the optical signals through the fibers 900 to a sensor system 1002. This system 1000 finds application with portable and handheld systems, that are described hereinbelow.

Figure 11:
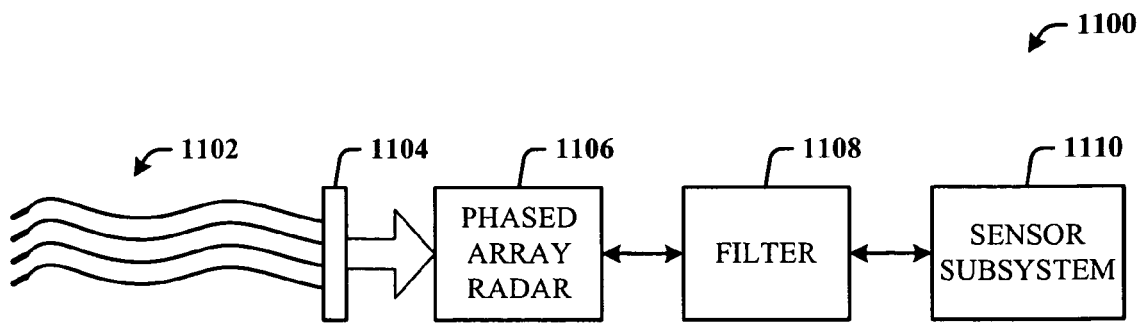
FIG. 11 illustrates an exemplary system that employs phased array radar technology as a means for communicating optical fiber change information data in accordance with the invention.

FIG. 11 illustrates an exemplary system 1100 that employs phased array radar technology 1102 as a means for communicating optical fiber change information data in accordance with the invention. The system 1100 employs multiple optical fibers 1102 as sensing means. Output image data of the fibers is preprocessed as a processing block 1104 in preparation for wireless image communication via the radar system 1106. Filters 1108 can be employed to further process the imaged change data, which filtered data is then processed at a sensor subsystem 1110. The use of multiple fibers the ends of which are bundled, cut and polished (or treated) for coupling photon signals from the change information facilitates capturing multiple photon signals that can be processed together to form the desired images (or data) for processing.

Figure 12:
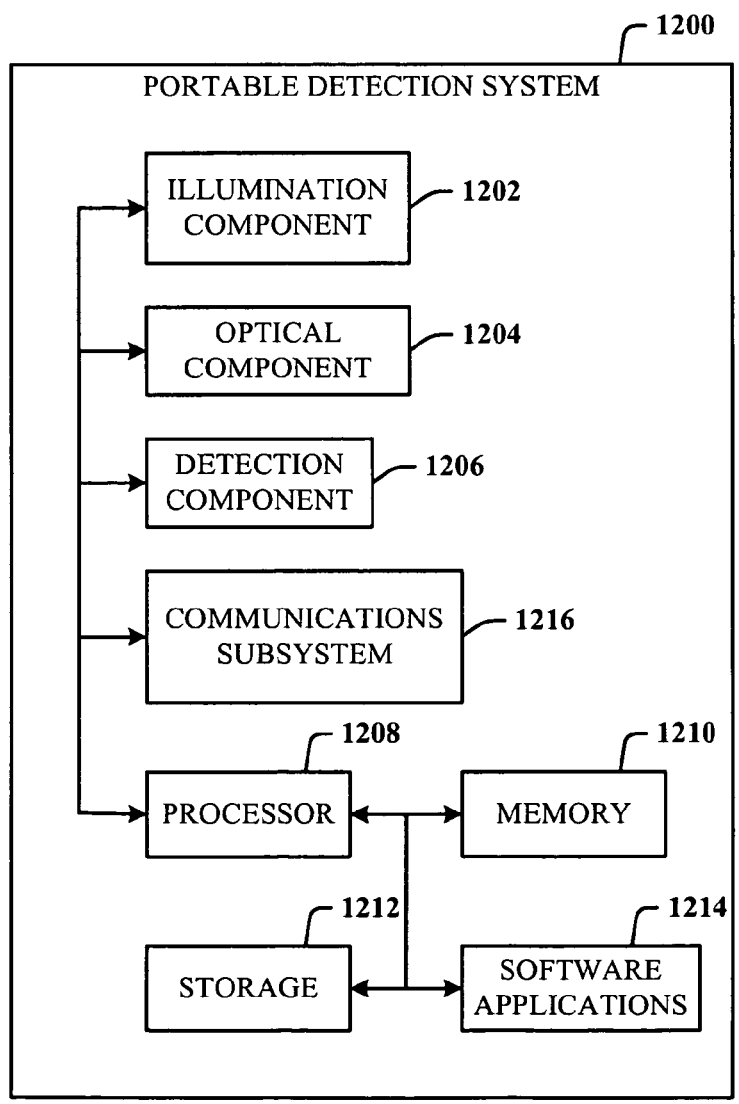
FIG. 12 illustrates a portable detection system of the subject invention.

FIG. 12 illustrates a portable detection system 1200 of the subject invention. The system 1200 includes an illumination component 1202 that illuminates a target according to the wavelength desired. An optical component 1204 senses change information of the vapor plume and/or particulate material of the target. The optical component 1204 can include any type of camera imaging system and suitable filters for optimizing signals that represent and convey the change information. A detection component 1206 receives image data from the optical component 1204 and processes change information (or lack thereof) contained in the image data to detect the desired target chemical(s).

A processor 1208 provides all onboard control and processing power for imaging processing and analysis of the system 1200. The system 1200 can further include memory 1210, mass storage 1212, and one or more software applications 1214 that support basic system operations, data processing, and component control and data acquisition for all onboard components. The system 1200 can also include a communications component 1216 that facilitates internal and external communications, both wired and wireless. In one implementation, the system 1200 can detect traces of explosives and/or drugs at a distance that ranges from about 10 feet to about 30 feet. In another implementation, the system 1200 detects trace amounts at a distance that ranges from about 5 feet to about 50 feet. In yet another implementation, the system 1200 can detect trace explosives and/or drugs at a distance that ranges from about 2 feet to about 500 feet.

Figure 13:
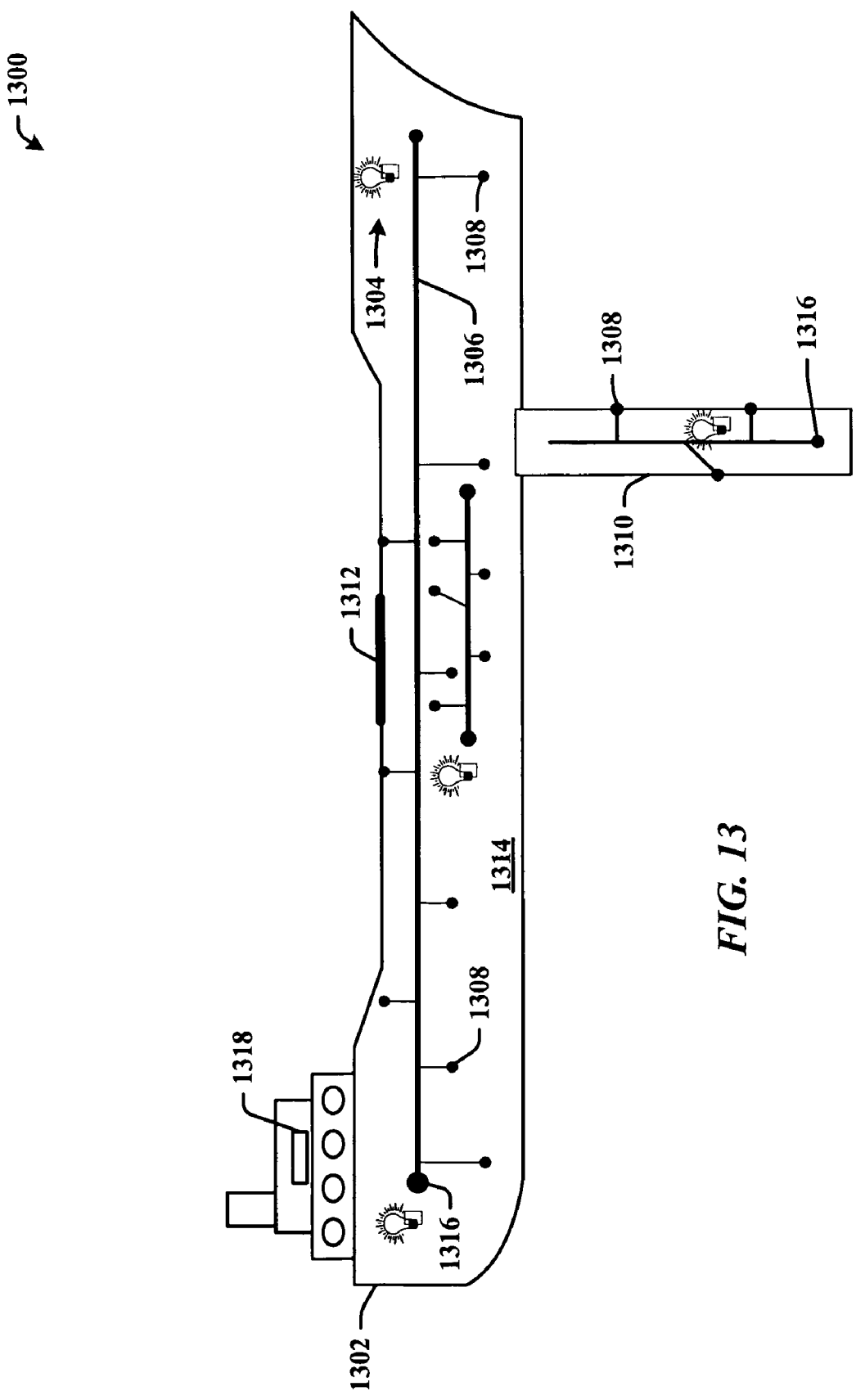
FIG. 13 illustrates a view of a concealed ship sensing and detection system in accordance with the invention.

FIG. 13 illustrates a view of a concealed sensing and detection system 1300 for a ship 1302 in accordance with the invention. In this particular implementation, the system 1300 includes light sources 1304, an optical fiber communications medium 1306, and a plurality of fiber and/or fiber/lens pairs 1308 strategically placed about the ship 1302 along the medium 1306 to monitor personnel boarding entrances 1310, cargo hold entrances 1312, and the cargo hold itself 1314. The optical fiber communications medium 1306 can also connect to an alert warning subsystem 1316 which includes a sensor monitor and transmitted subsystem that facilitates alerting the captain, a shipping port and/or other ships of the presence of drugs and/or explosives detected on the ship 1302.

The ship 1302 can also include an onboard process and analysis system 1318 that communicates with the alert warning subsystems 1316 in a wired and/or wireless manner. Note that there can be many independently operating sensing subsystems strategically placed through the ship 1302. For example, there can be a first independent system for the boarding entrance 1310, a second system for the hold entrance 1312, a third system for the cargo hold areas 1314, etc., each of which transmits change data (e.g., photoluminescence data) to the onboard process and analysis system 1318.

Figure 14:
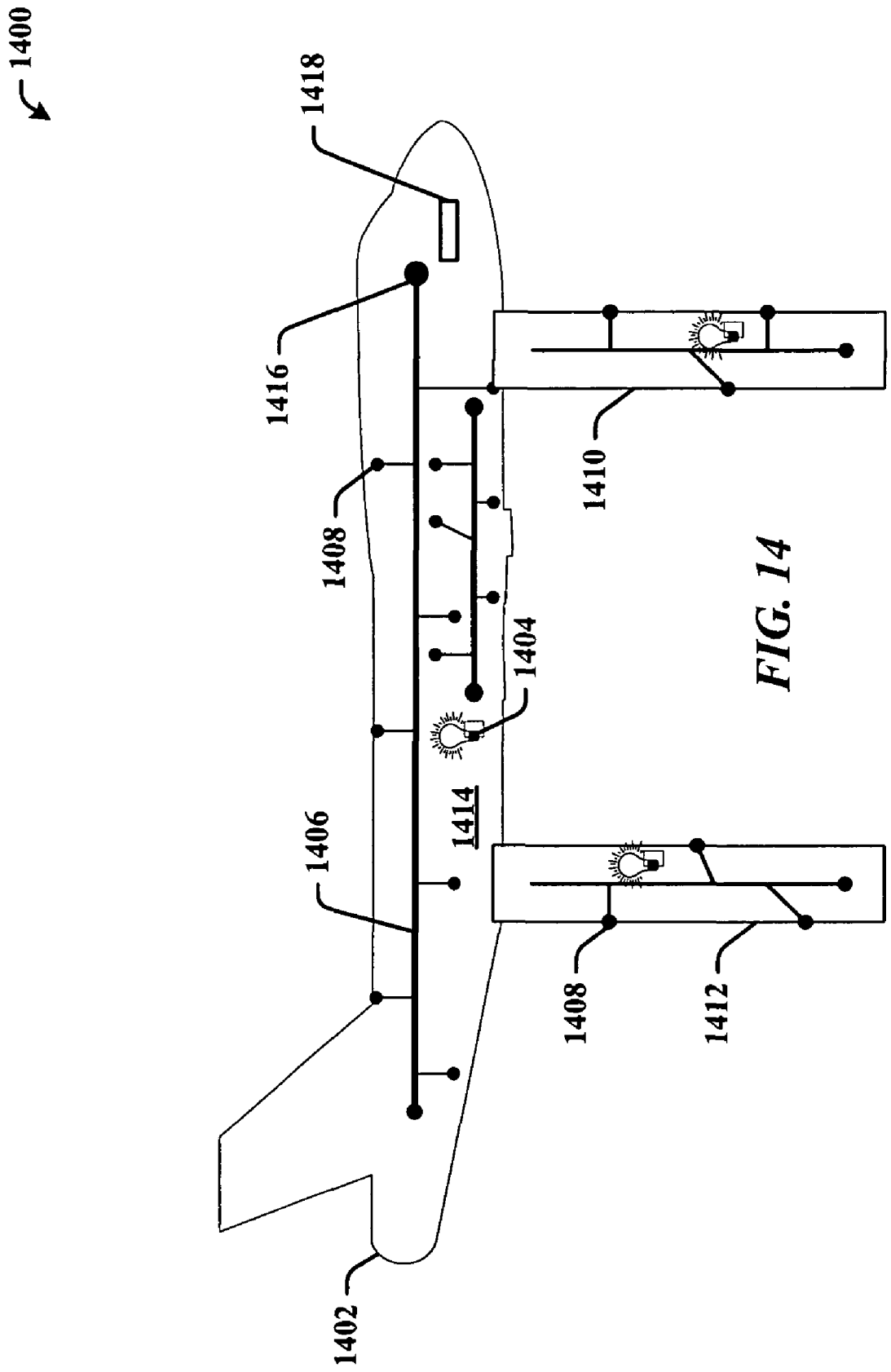
FIG. 14 illustrates a view of a concealed aircraft sensing and detection system in accordance with the invention.

FIG. 14 illustrates a view of a concealed sensing and detection system 1400 for an aircraft 1402 in accordance with the invention. In this particular implementation, the system 1400 includes light sources 1404, an optical fiber communications medium 1406, and a plurality of fiber and/or fiber/lens pairs 1408 strategically placed about the plane 1402 to monitor personnel boarding entrances 1410, cargo hold entrances 1412, and the cargo hold itself 1414. The optical fiber communications medium 1406 connects to an alert warning subsystem 1416 that can alert the captain and/or a ground control of the presence of drugs and/or explosives detected on the plane 1402. The plane 1402 can also include an onboard process and analysis system 1418 that communicates with the alert warning subsystem 1416 in a wired and/or wireless manner. Note that there can be many independently operating sensing subsystems strategically placed throughout the plane 1402. For example, there can be a first independent system for the boarding entrance 1410, a second system for the hold entrance 1412, a third system for the cargo hold areas 1414, etc., each of which transmits change data (e.g., photoluminescence signals) to the onboard process and analysis system 1418.

Figure 15:
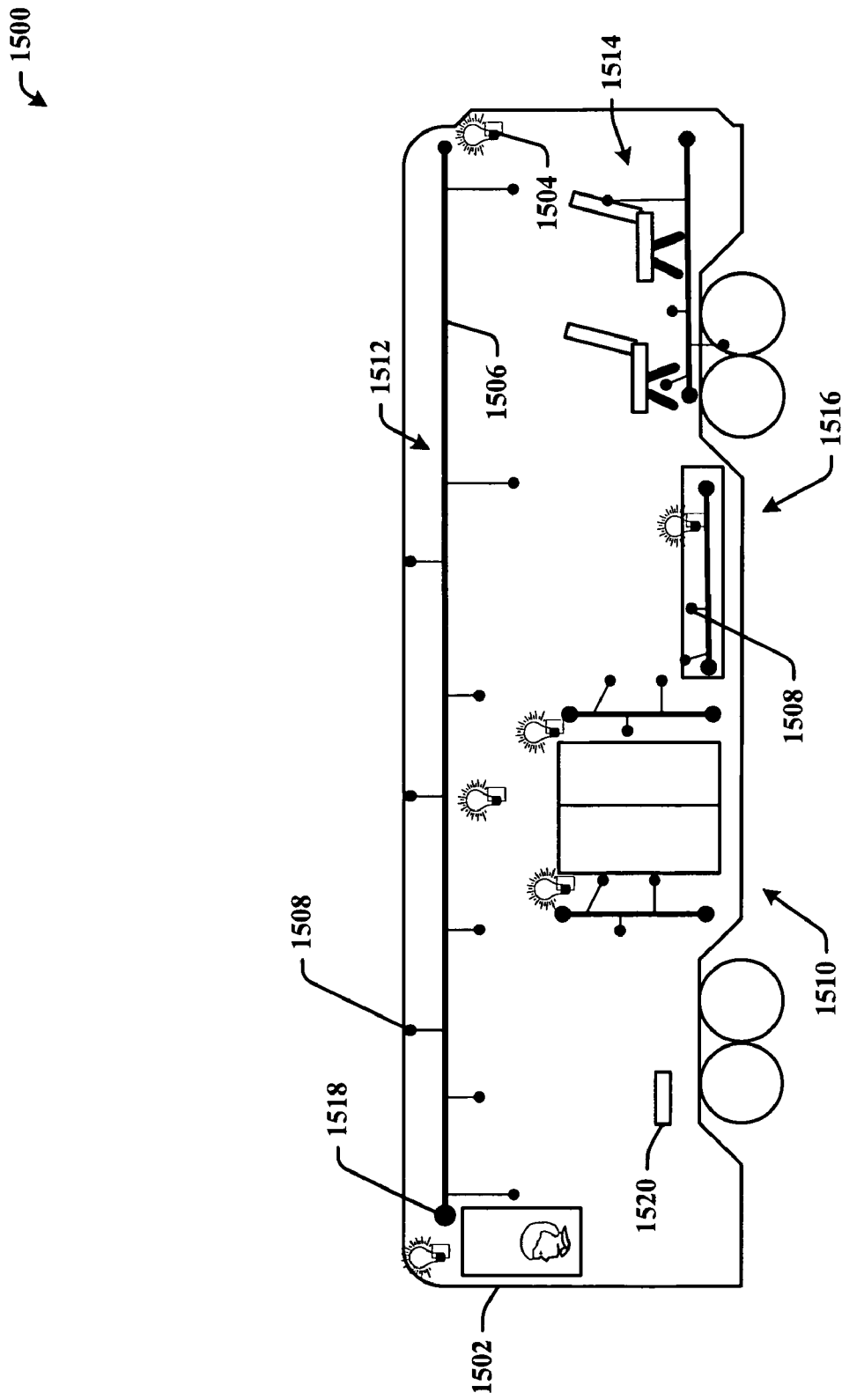
FIG. 15 illustrates a view of a concealed public transportation sensing and detection system in accordance with the invention.

FIG. 15 illustrates a view of a concealed sensing and detection system 1500 for a public transportation vehicle 1502 (e.g., a bus, trolley, or the like) in accordance with the invention. In this particular implementation, the system 1500 includes light sources 1504, an optical fiber communications medium 1506, and a plurality of fiber and/or fiber/lens pairs 1508 strategically placed about the vehicle 1502 to monitor personnel boarding entrances 1510, overhead luggage areas 1512, seating areas 1514 (e.g., seats, seat backs, underneath seats, . . . ), and underneath luggage and cargo areas 1516.

The optical fiber communications medium 1506 connects to an alert warning subsystem 1518 that can alert the driver and/or nearest police station of the presence of drugs and/or explosives detected on the vehicle 1502. The vehicle 1502 can also include an onboard process and analysis system 1520 that communicates with the alert warning subsystem 1518 in a wired and/or wireless manner. Note that there can be many independently operating sensing subsystems strategically placed throughout the vehicle. For example, there can be a first independent system for the boarding entrance 1510, a second independent system for the luggage/cargo area 1516, a third system for the overhead luggage area 1512, a fourth independent system for the seating areas 1514, etc., each of which transmits signals representative of the detected change data (e.g., photoluminescence, photofragmentation, . . . ) to the onboard process and analysis system 1520.

Figure 16:
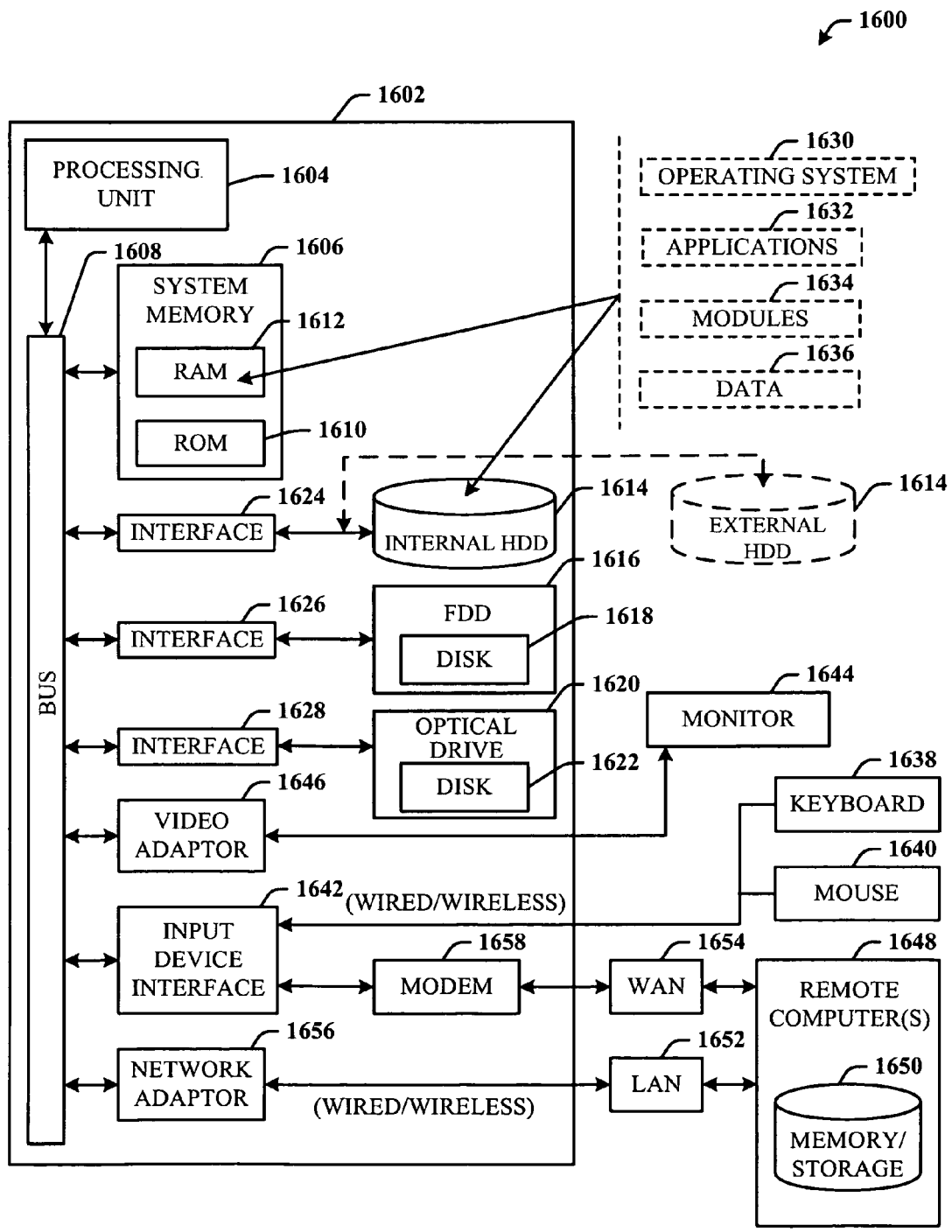
FIG. 16 illustrates a block diagram of a computer operable to provide processing, analysis, notification, and other functions for the disclosed covert and/or open illumination and detection architecture.

Referring now to FIG. 16, there is illustrated a block diagram of a computer operable to provide processing, analysis, notification, and other functions for the disclosed covert and/ or open illumination and detection architecture. In order to provide additional context for various aspects of the subject invention, FIG. 16 and the following discussion are intended to provide a brief, general description of a suitable computing environment 1600 in which the various aspects of the invention can be implemented. While the invention has been described above in the general context of computer-executable instructions that may run on one or more computers, those skilled in the art will recognize that the invention also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the invention may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and non-volatile media, removable and non-removable media. By way of example, and not limitation, computer-readable media can comprise computer storage media and communication media. Computer storage media includes both volatile and non-volatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 16, the exemplary environment 1600 for implementing various aspects of the invention includes a computer 1602, the computer 1602 including a processing unit 1604, a system memory 1606 and a system bus 1608. The system bus 1608 couples system components including, but not limited to, the system memory 1606 to the processing unit 1604. The processing unit 1604 can be any of various commercially available processors. Dual microprocessors and other multi-processor architectures may also be employed as the processing unit 1604.

The system bus 1608 can be any of several types of bus structure that may further interconnect to a memory bus (with or without a memory controller), a peripheral bus, and a local bus using any of a variety of commercially available bus architectures. The system memory 1606 includes read-only memory (ROM) 1610 and random access memory (RAM) 1612. A basic input/output system (BIOS) is stored in a non-volatile memory 1610 such as ROM, EPROM, EEPROM, which BIOS contains the basic routines that help to transfer information between elements within the computer 1602, such as during start-up. The RAM 1612 can also include a high-speed RAM such as static RAM for caching data.

The computer 1602 further includes an internal hard disk drive (HDD) 1614 (e.g., EIDE, SATA), which internal hard disk drive 1614 may also be configured for external use in a suitable chassis (not shown), a magnetic floppy disk drive (FDD) 1616, (e.g., to read from or write to a removable diskette 1618) and an optical disk drive 1620, (e.g., reading a CD-ROM disk 1622 or, to read from or write to other high capacity optical media such as the DVD). The hard disk drive 1614, magnetic disk drive 1616 and optical disk drive 1620 can be connected to the system bus 1608 by a hard disk drive interface 1624, a magnetic disk drive interface 1626 and an optical drive interface 1628, respectively. The interface 1624 for external drive implementations includes at least one or both of Universal Serial Bus (USB) and IEEE 1394 interface technologies. Other external drive connection technologies are within contemplation of the subject invention.

The drives and their associated computer-readable media provide nonvolatile storage of data, data structures, computer-executable instructions, and so forth. For the computer 1602, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules can be stored in the drives and RAM 1612, including an operating system 1630, one or more application programs 1632, other program modules 1634 and program data 1636. All or portions of the operating system, applications, modules, and/or data can also be cached in the RAM 1612. It is appreciated that the invention can be implemented with various commercially available operating systems or combinations of operating systems.

A user can enter commands and information into the computer 1602 through one or more wired/wireless input devices, e.g., a keyboard 1638 and a pointing device, such as a mouse 1640. Other input devices (not shown) may include a microphone, an IR remote control, a joystick, a game pad, a stylus pen, touch screen, or the like. These and other input devices are often connected to the processing unit 1604 through an input device interface 1642 that is coupled to the system bus 1608, but can be connected by other interfaces, such as a parallel port, an IEEE 1394 serial port, a game port, a USB port, an IR interface, etc.

A monitor 1644 or other type of display device is also connected to the system bus 1608 via an interface, such as a video adapter 1646. In addition to the monitor 1644, a computer typically includes other peripheral output devices (not shown), such as speakers, printers, etc.

The computer 1602 may operate in a networked environment using logical connections via wired and/or wireless communications to one or more remote computers, such as a remote computer(s) 1648. The remote computer(s) 1648 can be a workstation, a server computer, a router, a personal computer, portable computer, microprocessor-based entertainment appliance, a peer device or other common network node, and typically includes many or all of the elements described relative to the computer 1602, although, for purposes of brevity, only a memory/storage device 1650 is illustrated. The logical connections depicted include wired/wireless connectivity to a local area network (LAN) 1652 and/or larger networks, e.g., a wide area network (WAN) 1654. Such LAN and WAN networking environments are commonplace in offices and companies, and facilitate enterprise-wide computer networks, such as intranets, all of which may connect to a global communications network, e.g., the Internet.

When used in a LAN networking environment, the computer 1602 is connected to the local network 1652 through a wired and/or wireless communication network interface or adapter 1656. The adaptor 1656 may facilitate wired or wireless communication to the LAN 1652, which may also include a wireless access point disposed thereon for communicating with the wireless adaptor 1656.

When used in a WAN networking environment, the computer 1602 can include a modem 1658, or is connected to a communications server on the WAN 1654, or has other means for establishing communications over the WAN 1654, such as by way of the Internet. The modem 1658, which can be internal or external and a wired or wireless device, is connected to the system bus 1608 via the serial port interface 1642. In a networked environment, program modules depicted relative to the computer 1602, or portions thereof, can be stored in the remote memory/storage device 1650. It will be appreciated that the network connections shown are exemplary and other means of establishing a communications link between the computers can be used.

The computer 1602 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11x (a, b, g, etc.) to provide secure, reliable, fast wireless connectivity. A Wi-Fi network can be used to connect computers to each other, to the Internet, and to wired networks (which use IEEE 802.3 or Ethernet).

Wi-Fi networks can operate in the unlicensed 2.4 and 5 GHz radio bands. IEEE 802.11 applies to generally to wireless LANs and provides 1 or 2 Mbps transmission in the 2.4 GHz band using either frequency hopping spread spectrum (FHSS) or direct sequence spread spectrum (DSSS). IEEE 802.11a is an extension to IEEE 802.11 that applies to wireless LANs and provides up to 54 Mbps in the 5 GHz band. IEEE 802.11a uses an orthogonal frequency division multiplexing (OFDM) encoding scheme rather than FHSS or DSSS. IEEE 802.11b (also referred to as 802.11 High Rate DSSS or Wi-Fi) is an extension to 802.11 that applies to wireless LANs and provides 11 Mbps transmission (with a fallback to 5.5, 2 and 1 Mbps) in the 2.4 GHz band. IEEE 802.11g applies to wireless LANs and provides 20+Mbps in the 2.4 GHz band. Products can contain more than one band (e.g., dual band), so the networks can provide real-world performance similar to the basic 10BaseT wired Ethernet networks used in many offices. Other systems such as Wi-Max and Bluetooth can be employed.

What has been described above includes examples of the invention. It is, of course, not possible to describe every conceivable combination of components or methodologies for purposes of describing the subject invention, but one of ordinary skill in the art may recognize that many further combinations and permutations of the invention are possible. Accordingly, the invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A sensing and detection system for detecting materials of interest associated with transportation by water, comprising:
   an illumination component of a watercraft for imposing electromagnetic energy on targets located throughout the watercraft;
   a sensing component of the watercraft for automatically scanning the targets for presence of materials of interest;
   an optical receiving component of the watercraft for receiving photoluminescent information representative of a change in a chemical component of the materials of interest; and
   a notification component of the watercraft for generating a notification signal in response to sensing one or more of the materials of interest.

2. The system of claim 1, wherein the illumination component further comprises light sources strategically placed about the watercraft that illuminate the targets for the materials of interest.

3. The system of claim 1, wherein the sensing component further comprises an optical fiber communications medium and fiber/lens pairs strategically placed about the watercraft.

4. The system of claim 1, wherein the sensing component is concealed within the watercraft.

5. The system of claim 1, wherein the sensing component further comprises independently operating sensing subsystems strategically placed throughout the watercraft.

6. The system of claim 5, wherein the independently operating sensing subsystems comprise an independent subsystem located in at least one of a boarding entrance, a hold entrance, or a cargo hold area.

7. The system of claim 1, wherein the notification component comprises an alert warning subsystem for alerting at least one of watercraft personnel or ground control personnel of the presence of the materials of interest detected on the watercraft.

8. The system of claim 1, further comprising an onboard process and analysis system that receives wireless signals from the sensing component, to be processed for the notification component.

9. The system of claim 1, wherein the materials of interest comprise at least one of drugs, explosives, or related components thereof.

10. A system for sensing materials of interest in a watercraft environment, comprising:
- a watercraft for transporting at least one of people or articles;
- an illumination component as part of the watercraft that automatically imposes electromagnetic energy of a predetermined wavelength on the at least one of people or articles for detecting presence of drugs or explosives;
- a sensing component as part of the watercraft that senses change information due to the electromagnetic energy contacting at least one of vapors or particles associated with the presence of the drugs or explosives;
- an optical component of the sensing component for receiving photon signals representative of the change information;
- a detection component as part of the watercraft for processing the photon signals and outputting detection data indicative of the presence of the drugs or explosives; and
- a notification component as part of the watercraft that transmits a notification signal in response to the detection data.

11. The system of claim 10, wherein the sensing component is configured to monitor at least one of boarding entrances, cargo hold entrances, or a cargo hold of the watercraft.

12. The system of claim 10, further comprising an analysis component for performing analysis on the detection data received from the detection component, the analysis comprising at least one of image analysis, color analysis, timing analysis, or signal conditioning.

13. The system of claim 10, further comprising a central monitor and control system for controlling at least one of tuning a light source to a predetermined frequency, orienting the light source in a predetermined direction, conducting onboard tests, or managing power subsystems on/off and in reduced power modes.

14. The system of claim 10, further comprising a communications component that facilitates at least one of wired or wireless communications between at least one of the illumination component, sensing component, the detection component, optical component, detection component, or notification component.

15. The system of claim 10, wherein at least one of the illumination component, sensing component, the detection component, optical component, detection component or notification component are covertly deployed for concealed sensing and detection of the drugs or explosives.

16. A method of sensing materials of interest in a watercraft environment, comprising:
- illuminating an area of a watercraft with electromagnetic energy of a predetermined wavelength;
- detecting photon signals representative of change information in the electromagnetic energy indicative of presence of at least one of drugs or explosives in the area of the watercraft; and
- transmitting a notification signal in response to the change information.

17. The method of claim 16, further comprising detecting a change in frequency of the electromagnetic radiation that is indicative of the presence of the at least one of drugs or explosives in the area of the watercraft.

18. The method of claim 16, further comprising monitoring at least one of boarding entrances, cargo hold entrances, or a cargo hold of the watercraft based on illumination and detection.

19. The method of claim 16, further comprising alerting at least one of watercraft personnel or control personnel of the presence of the drugs or explosives detected on the watercraft as part of transmitting the notification signal.

20. The method of claim 16, further comprising performing analysis on the photon signals, the analysis comprising at least one of image analysis, color analysis, timing analysis, or signal conditioning.

* * * * *